United States Patent [19]
Chapuis et al.

[11] Patent Number: 5,696,075
[45] Date of Patent: Dec. 9, 1997

[54] CAMPHOLINIC ALDEHYDE DERIVATIVES, PROCESS FOR THEIR PREPARATION AND THEIR USE AS PERFUMING INGREDIENTS

[75] Inventors: Christian Chapuis, Mies; Pierre-Alain Blanc, Crassier, both of Switzerland

[73] Assignee: Firmenich SA, Geneva, Switzerland

[21] Appl. No.: 507,896

[22] Filed: Jul. 27, 1995

[30] Foreign Application Priority Data

Jul. 28, 1994 [CH] Switzerland ............... 2385/94

[51] Int. Cl.$^6$ ............................................. A61K 7/46
[52] U.S. Cl. .................. 512/6; 512/8; 512/6; 564/253; 558/432; 568/446; 568/838
[58] Field of Search ............. 512/6, 8; 564/253; 558/432; 568/446, 838

[56] References Cited

U.S. PATENT DOCUMENTS 5,504,066  4/1996  Market et al. ..................... 512/8

FOREIGN PATENT DOCUMENTS 0 155 591  5/1988  European Pat. Off.
A-4131119  3/1993  Germany
WO 93/21142  10/1993  WIPO

*Primary Examiner*—Johann Richter
*Assistant Examiner*—Laura L. Stockton
*Attorney, Agent, or Firm*—Pennie & Edmonds LLP

[57] ABSTRACT

Described herein are compounds of the formula

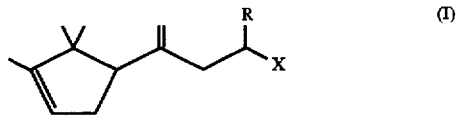

(I)

wherein R represents a hydrogen atom or a methyl radical and X stands for a —CHO, or a —CN group, are useful as perfuming ingredients for preparing perfuming compositions and a variety of perfumed articles, to which they impart sandalwood-type odor notes, together with marine, ozone type odor characters, such that said compositions and articles thus acquire a "transparent" connotation. The aldehydes of formula (I) are also useful as starting products for the preparation of the corresponding fragrant alcohols and nitriles.

13 Claims, No Drawings

CAMPHOLINIC ALDEHYDE DERIVATIVES, PROCESS FOR THEIR PREPARATION AND THEIR USE AS PERFUMING INGREDIENTS

BRIEF SUMMARY OF THE INVENTION

The present invention relates to a compound of formula

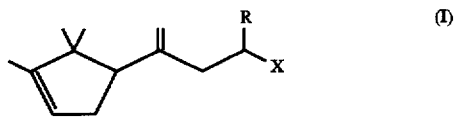

wherein R represents hydrogen or a methyl radical and X stands for a —CHO, or —C≡N group.

Another object of the invention is a method to confer, improve, enhance or modify the odor properties of a perfuming composition or a perfumed article, which method comprises adding the compound above-mentioned to said composition or article.

The invention further provides perfuming compositions and perfumed articles containing said compound (I) as active perfuming ingredient.

A further object of the invention is a method to confer, improve, enhance or modify the sandalwood, marine, ozone type odor character of a perfuming composition or a perfumed article, which method comprises adding thereto (−)-(1′R)-2-methyl-4-(2′,2′,3′-trimethyl-3′-cyclopenten-1′-yl)-4-penten-1-al or (+)-(1′S)-4-(2′,2′,3′-trimethyl-3′-cyclopenten-1′-yl)-4-penten-1-al.

The invention also concerns a process for the preparation of a compound of formula

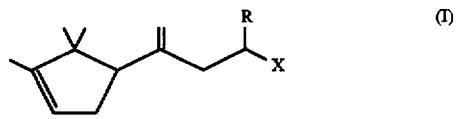

wherein R represents hydrogen or a methyl radical and X stands for a —CHO, or —C≡N group, which process comprises thermally treating an ether of formula

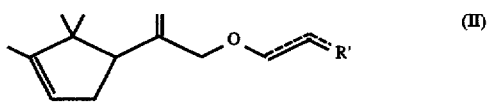

having a double bond in one of the positions indicated by the dotted lines and wherein R′ represents hydrogen, a methyl radical or a methylene radical, under appropriate conditions and at a temperature sufficient to form an aldehyde of formula

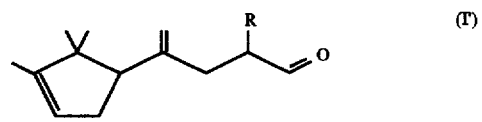

wherein R represents hydrogen or a methyl radical and, if necessary, converting said aldehyde into the corresponding nitrile, in a generally known manner.

The ethers of formula (II), used as starting products in this process and the intermediate oximes of the aldehydes (I′), are also an object of the invention.

BACKGROUND OF THE INVENTION

The invention relates to the field of perfumery and, more particularly, to that of the odoriferous compounds derived from campholenic aldehyde.

A large number of this type of compounds has been described in the prior art, namely a number of alcohols characterized by sandalwood type odors. This results from the fact that, in spite of the abundance of such compounds already known and the individual contribution that each of them is able to bring to the olfactive reconstitution of the characters of natural sandalwood oil, the typical odor of the latter cannot be replaced through the addition of anyone of these compounds, nor indeed of a mixture of several of said compounds. This explains why research in this field remains unflagging, new products being regularly discovered and added to the performer's palette in this area of fragrances.

One such example is a recent publication, i.e. International patent application n° WO 93/21142, which describes compounds of formula

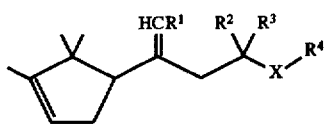

wherein, independently from each other, $R^1$ represents hydrogen or a methyl radical, $R^2$ and $R^3$ are hydrogen or an alkyl radical having from 1 to 5 carbon atoms, $R^4$ is hydrogen or a $CHR^5R^6$ group, in which $R^5$ and $R^6$ represent hydrogen or an alkyl radical having from 1 to 6 carbon atoms, and X represents a CO or CHOH group, with the proviso that a) at least one of the symbols $R^2$ and $R^3$ represents an alkyl radical and b) 2-methyl-4-(2,2,3-trimethyl-3-cyclopenten-1-yl)-4-penten-1-ol is excluded.

It is also indicated in this document that the compounds wherein $R^2$ and $R^3$ are both alkyl groups are preferred to their homologues which have one of these symbols representing hydrogen, since the sandalwood odor of the first is more powerful than that of the latter.

The formula above, disclosed in this prior art document, has a very general character; in fact, it can be construed to include hundreds of compounds, and namely 2-methyl-4-(2′,2′,3′-trimethyl-3′-cyclopenten-1′-yl)-4-penten-1-al, one of the compounds which are the object of the present disclosure. However, it is quite clear from the description of the cited document that its authors failed to recognize the potential value of this compound. Not only did they omit to describe it specifically but, it is also patently clear that, in accordance with the preference indicated for the species which are doubly substituted in the side chain, the authors clearly concentrated themselves on the preparation of the latter, and more specifically of the ketonic and hydroxylic variants thereof, as is apparent from the specific examples there-disclosed. Furthermore, apart from the preference above-mentioned, there is strictly no suggestion that any particular compound, amongst all those that the formula may potentially include, could have distinct and very particular odor properties. This document, therefore, provides no guidance nor suggestion that could have led to the presently disclosed result, i.e. that 2-methyl-4-(2′,2′,3′-trimethyl-3′-cyclopenten-1′-yl)-4-penten-1-al possesses truly surprising and original odor properties and presents an olfactive behaviour that is quite distinct from that of the prior known analogues and in fact even uncharacteristic in view of the prior art. Yet, this is exactly what we have observed.

DETAILED DESCRIPTION OF THE INVENTION

A first object of the invention is therefore a compound of formula (I) as described above.

Amongst said compounds, we have now discovered that 2-methyl-4-(2',2',3'-trimethyl-3'-cyclopenten-1'-yl)-4-penten-1-al, and more particularly its chiral isomer of (–)-(1'R) configuration, a preferred compound of the invention, possesses an unexpected odor in view of the prior knowledge regarding the odor properties of campholenic aldehyde derivatives. It develops a woody-sandalwood type odor note, slightly aldehydic, which is more reminiscent of the cedar-pine odor connotation than of the sandalwood type one, which note is combined with a distinct marine, ozone character. The latter is reinforced in the bottom note, which is strongly ozone-marine-like, recalling the odor of seaweeds. Such a combination of odor characters is quite unexpected in view of the prior art and namely of the document cited above. Nothing in this document could have made it possible to even suspect that this compound would possess such valuable qualities. As a result of the latter, this compound can in fact bring to the sandalwood notes a valued aqueous and marine aspect, with a particularly marked and fresh effect in the headnotes. It therefore imparts to the compositions into which it is incorporated the so-called "transparent" odor effect characteristic of the marine notes, which is at present very much appreciated by the consumers and known in the perfumes with a green or floral connotation, but totally unknown in the fragrances with a woody-sandalwood character. In addition, the odor of this compound has a good strength and tenacity.

Moreover, the presence of these marine, ozone, seaweed characters in the odor of this type of compounds seems to be very rare indeed since, in spite of the large number of homologues and analogue compounds that we prepared throughout the studies which led to this unexpected result, only a lower homologue of the compound above-cited, i.e. 4-(2',2',3'-trimethyl-3'-cyclopenten-1'-yl)-4-penten-1-al, turned out to possess a slightly aqueous odor character which, curiously, is no longer combined with sandalwood notes, but with totally distinct odor notes, the nature of which, in addition, is not identical in the two chiral isomers of this compound. Thus, (–)-(1'R)-4-(2',2',3'-trimethyl-3'-cyclopenten-1'-yl)-4-penten-1-al develops a fragrance further possessing an aldehydic note, reminiscent of citronellal, citrusy, spicy, recalling the odor of the citronella leaves. As to its bottom note, it has a character which is reminiscent of the odor of 3-(4-tert-butyl-1-phenyl)-2-methylpropanal, but with an even greener connotation and a slightly orangy aspect. Its enantiomer, or (+)-(1'S)-4-(2',2',3'-trimethyl-3'-cyclopenten-1'-yl)-4-penten-1-al, is provided with a more metallic and aldehydic odor, recalling that of trans-4-decenal, and the bottom note of which is more floral and even stronger in the aqueous character. The use of this latter compound to enhance the latter odor character in perfumed compositions and articles is in fact preferred to that of its enantiomer above-cited.

On the other hand, the nitriles of formula (I) no longer possess this marine aspect in their odor. For example, 2-methyl-4-(2',2',3'-trimethyl-3'-cyclopenten-1'-yl)-4-pentenenitrile, and more particularly its more preferred isomer of (–)-(1'R) configuration, possesses a woody-citrus, fruity and slightly fatty odor. The citrus, fruity and fresh character is further enhanced in the odor of (–)-(1'R,2R)-2-methyl-4-(2',2',3'-trimethyl-3'-cyclopenten-1'-yl)-4-pentenenitrile and accompanied of a sandalwood bottom character. This compound is, moreover, preferred, from an olfactive point of view, to its diastereomer of (–)-(1'R,2S) configuration which has a sandalwood odor wherein the desired fruity-citrus character is no longer present.

The compounds of the invention are a representative example of the unpredictability of olfactive behaviour on the basis of structural similarity. In fact, not only do they possess distinct fragrances from those of prior known analogues, but differences are also found between the various claimed compounds and even amongst the chiral isomers of a same compound.

As a result of their odor properties, the compounds of the invention are convenient for the preparation of perfuming compositions and perfumed articles which are also the object of the invention. They are useful for both fine and technical perfuming applications, since they can be used for perfuming articles as varied as perfumes and colognes, soaps, bath or shower gels, shampoos or other hair-care products, body deodorants or air-fresheners, detergents or fabric softeners, or yet household products. In these applications, they can be used either on their own, or, as is more usual in perfumery, in admixture with other perfuming ingredients, solvents or adjuvants of current use in perfumery and which can easily be chosen by the skilled person as a function of the desired fragrance and of the nature of the product to be perfumed. A detailed description of such ingredients is not warranted here and one can cite as typical examples ingredients such as those described in reference textbooks of which the work of S. Arctander, Perfume and Flavour Chemicals, Montclair, N.J. USA (1969) is quite representative.

The concentrations in which the compounds of the invention can be used to impart the desired perfuming effects vary in a wide range of values, which, as is well-known, depend on both the nature of the product one desires to perfume and the required odor effect, as well as on the nature of the other perfuming co-ingredients present in a given composition. Thus, concentrations of the order of 1 to 5%, or say 10 or even 20% by weight of compound of the invention, relative to the weight of the composition, are quite appropriate when the cited compounds are added to a variety of perfuming compositions. Distinctly inferior concentration values will normally be used when employing these compounds for perfuming the varied articles cited above.

The compounds (I) of the invention are prepared by an original process which is also the object of the invention and according to which an ether of formula

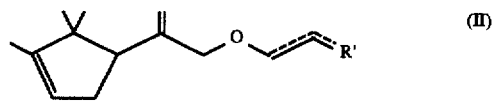

having a double bond in one of the positions indicated by the dotted lines and wherein R' represents hydrogen, a methyl radical or a methylene radical, is subjected to a thermal treatment under the appropriate conditions to provide the aldehyde of formula (I') mentioned earlier, which can then be converted into the corresponding nitrile by conventional methods.

The thermal treatment which characterizes the process of the invention is a Claisen type rearrangement reaction which takes place at temperatures of between about 160° and 240° C. The starting ethers (II) are novel compounds which can be prepared by etherification of 2-(2',2',3'-trimethyl-3'-cyclopenten-1'-yl)-2-propen-1-ol under the conditions described further on.

According to a particular embodiment of the process of the invention, which turns out to be advantageous for preparing 2-methyl-4-(2',2',3'-trimethyl-3'-cyclopenten-1'-yl)-4-penten-1-al, 4-[1-(allyloxymethyl)-ethenyl]-1,5,5-trimethyl-1-cyclopenten is thermally treated in the presence of a catalyst, to provide said 2-methyl-4-(2',2',3'-trimethyl-3'-cyclopenten-1'-yl)4-penten-1-al.

As the catalyst, there can be used Pd/C or Rh/C for example, or yet tris(triphenylphosphine)ruthenium dichloride. The reaction takes place at a temperature varying in a considerably wide range of values, for instance from 130° to 250° C. Likewise, the catalyst can be used in a range of concentrations varying between 0.05 and 0.5 mole %, with regard to the starting ether. Enhanced yields were obtained when the catalyst was used at a concentration comprised between 0.05 and 0.2 mole %. Depending on the type of catalyst used, the reaction may be carried out in the absence of a solvent, as in the case of tris(triphenylphosphine) ruthenium dichloride, or in the presence of a suitable dilution medium selected amongst currently used solvents in this type of reaction. For example, when using Pd/C or Ru/C, we found it advantageous to use mesitylene as solvent. Alternatively, toluene under pressure was also a convenient medium.

This advantageous embodiment of the process of the invention makes it possible to synthesize the abovementioned pentenal in one pot, starting from the cited allylic ether (II), the preparation of which is more straightforward and economical than that of its isomer 1,5,5-trimethyl-4-[1-(1-propenyloxymethyl)ethenyl]-1-cyclopenten, which possesses the double bond in the intermediate position. The 4-[1-(allyloxymethyl)ethenyl]-1,5,5-trimethyl-1-cyclopenten, a novel compound, is in fact prepared by allylation, by means of allyl bromide, of the abovementioned 2-(2',2',3'-trimethyl-3'-cyclopenten-1'-yl)-2-propen-1-ol, under the conditions which are described in detail further on. When this ether undergoes heating in the presence of the catalyst, it is first converted to its isomer 1,5,5-trimethyl-4-[1-(1-propenyloxymethyl)ethenyl]-1-cyclopenten mentioned above, which then undergoes Claisen rearrangement to form the desired aldehyde.

It goes without saying that the use of 2-(2',2',3'-trimethyl-3'-cyclopenten-1'-yl)-2-propen-1-ol in the form of one or the other of its (−)-(S) and (+)-(R) chiral isomers, which isomers can be obtained from the corresponding pure enantiomers of campholenic aldehyde following the method described in EP 155 591, allows the preparation of the corresponding chiral isomers of ethers (II), and subsequently of aldehydes (I'), via the process of the invention.

The latter aldehydes (I') can then be used as starting products for the preparation of the nitriles of formula (I) according to the invention. This conversion can be obtained via conventional reactions, typically through the intermediate oxime of the starting aldehyde, which oxime is then reacted with a dehydrating agent, for example acetic anhydride. The reaction can be a one-pot process, carried out under known conditions described in detail further on, or, alternatively, the intermediate oxime, which is a novel compound, can be prepared and isolated first and subsequently reacted with the dehydrating agent.

Dehydrating agents other than the one cited above can of course be used. Detailed specification of such reagents is here superfluous, as this type of reaction is well-known to the skilled person [see, for example, J. March, Advanced Organic Chemistry: Reactions, Mechanisms and Structure, 3rd ed., sections 6–21 and 740, John Wiley & Sons, USA (1985)].

The aldehydes (I') according to the invention are also useful to prepare the corresponding fragrant alcohols. Since the above-described process of the invention allows the preparation of these aldehydes in a pure optical form, it is thus possible to obtain the pure chiral isomers of said alcohols. Following a particular embodiment of the process of the invention, (−)-(1'R)-, respectively (+)-(1'S)-2-methyl-4-(2',2',3'-trimethyl-3'-cyclopenten-1'-yl)-4-penten-1-al is thus further converted into the corresponding alcohol by means of a reducing agent.

This novel compound (I') thus opens a new and advantageous route for preparing the fragrant 2-methyl-4-(2',2',3'-trimethyl-3'-cyclopenten-1'-yl)-4-penten-1-ol described in EP 155 591. According to this prior art reference, the latter alcohol was in fact prepared as is described in Scheme I here-below:

SCHEME I

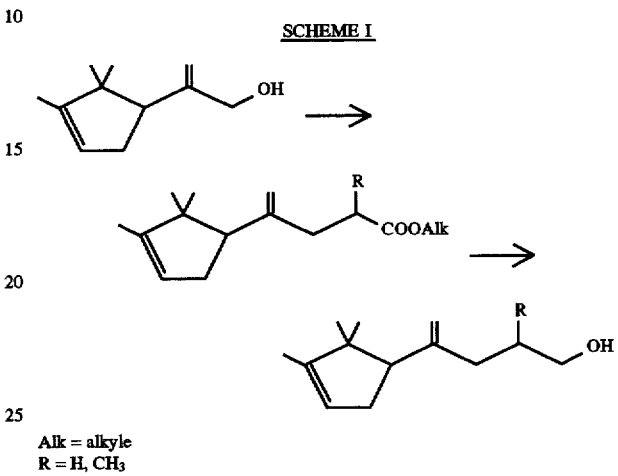

Alk = alkyle
R = H, CH₃

In spite of the utility and merits of this known process, we have now discovered that using 2-methyl-4-(2',2',3'-trimethyl-3'-cyclopenten-1'-yl)-4-penten-1-al according to the invention, in lieu of ethyl 2-methyl-4-(2',2',3'-trimethyl-3'-cyclopenten-1'-yl)-4-pentenoate, one of the intermediate esters in this scheme, provides an improved synthesis of said pentenol, presenting several advantages over the known process. This comes from the fact that the presently described novel method not only avoids the excess of hydride in the final phase of the preparation of said pentenol, which resulted from the reduction of the mentioned ester by means of LiAlH₄, but also makes it possible to suppress the use of ethyl orthopropionate, a very expensive compound which was required to prepare the mentioned ester, or ethyl 2-methyl-4-(2',2',3'-trimethyl-3'-cyclopenten-1'-yl)-4-pentenoate.

Furthermore, according to the process of the invention, and unlike what was the case with the prior art process, one can now use as reducing agent any current reagent known to be capable of converting aldehydes into alcohols, and this allows the choice of reducing agents which are cheaper than LiAlH₄.

Clearly, the use of 2-methyl-4-(2',2',3'-trimethyl-3'-cyclopenten-1'-yl)-4-penten-1-al in the form of one of its enantiomers of (−)-(1'R) or (+)-(1'S) configuration provides the corresponding optically active isomers of 2-methyl-4-(2',2',3'-trimethyl-3'-cyclopenten-1'-yl)-4-penten-1-ol.

The pentenol above-mentioned was described in EP 155 591, wherein it is indicated that it possesses an odor which is reminiscent of that of natural sandalwood essential oil. In addition, an optically active isomer thereof, i.e.(−)-2-methyl-4-(2',2',3'-trimethyl-3'-cyclopenten-1'-yl)-4-penten-1-ol was also described therein, but no mention of its specific odor properties can be found in this reference. In fact, despite the intrinsic olfactive value of each of the isomers, we have now established that their odor properties differ from one isomer to the next. Furthermore, it has now been discovered that the particular isomer mentioned hereabove possesses an odor which is more reminiscent of the scent of sandalwood essential oil than that of its enantiomer characterised by a positive optical rotation.

In addition, each of these enantiomers is a mixture of two diastereomers, as a result of the two possible orientations of the methyl substituent in the side chain. Thus, 2-methyl-4-(2',2',3'-trimethyl-3'-cyclopenten-1'-yl)-4-penten-1-ol can assume a total of four diastereomeric forms, which are in fact compounds never disclosed heretofore. It has turned out that, amongst the four, there is one species which is preferred by the perfumers, i.e. (−)-(1'R,2R)-2-methyl-4-(2',2',3'-trimethyl-3'-cyclopenten-1'-yl) -4-penten-1-ol of formula

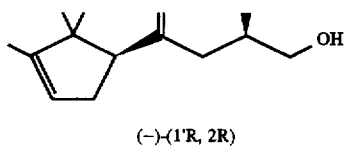

(−)-(1'R, 2R)

as a result of its more elegant and powerful sandalwood note. As for its diastereomer of (−)-(1'R,2S) configuration having the formula

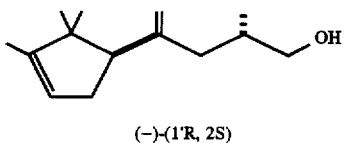

(−)-(1'R, 2S)

its sandalwood note is not as powerful but is accompanied of a more marked woody-cedar character. Furthermore, both diastereomers are more prized than their respective enantiomers, i.e. the compounds of (+)-(1'S,2S) and (+)-(1'S,2R) configurations of formulae

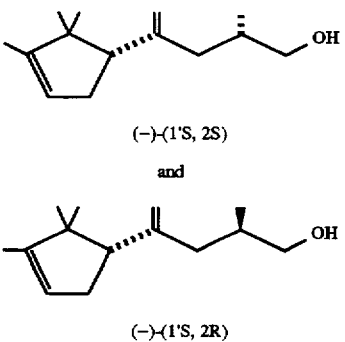

(−)-(1'S, 2S)

and (−)-(1'S, 2R)

the odors of which are less rich in the precious "lait de santal" type odor character. This rather seems to explain the fact mentioned above, i.e. that the perfumers also favor the mixtures of the two first mentioned diastereomers, constituting (−)-(1'R)-2-methyl-4-(2',2',3'-trimethyl-3'-cyclopenten-1'-yl) -4-penten-1-ol of formula

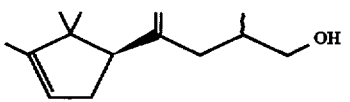

over the mixtures of the other two diastereomers, which form (+)-(1'S)-2-methyl-4-(2',2',3'-trimethyl-3'-cyclopenten-1'-yl)-4-penten-1-ol of formula

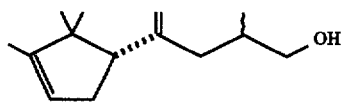

The four novel compounds here-above mentioned, whose individual odor qualities were totally unsuspected up until now, make it possible to prepare perfumed compositions with improved fragrances over those of the prior described ones, for example by varying at will the concentration of the preferred isomer of (−)-(1'R,2R) configuration present in the mixtures of two or more diastereomers which have been currently used heretofore as perfuming ingredients in said compositions, or even by simply adding said preferred isomer directly to these compositions.

In this context, it is interesting to point out that the use of the (−)-(1'R)-2-methyl-4-(2',2',3'- trimethyl-3'-cyclopenten-1'-yl) -4-penten-1-al according to the invention to prepare the corresponding optically active alcohol, or (−)-(1'R)-2-methyl-4-(2',2',3'-trimethyl-3'-cyclopenten-1'-yl)- 4-penten-1-ol, presents a further advantage over that of the known process described in EP 155 591 and illustrated in Scheme I. It has in fact turned out that the above-mentioned optically active pentenal can be more easily epimerized than the intermediate optically active ester in the known process, to be thus enriched in the diastereomer of 2R configuration useful for preparing the preferred diastereomer of the corresponding alcohol. The presently disclosed aldehyde, therefore, has the further advantage of allowing the preparation of an improved quality of this perfuming alcohol at an industrial scale, and this through a process which uses cheaper and less complex reagents than the prior art method.

The invention will now be described in further detail by way of the following examples, wherein the temperatures are indicated in degrees centigrade and the abbreviations have the usual meaning in the art.

EXAMPLE 1

Preparation of (−)-(1'R)-2-methyl-4-(2',2',3'-trimethyl-3'-cyclopenten-1'-yl) -4-penten-1-al A. In one pot, starting from (−)-(S)-4-[1-(allyloxymethyl) ethenyl]-1,5,5-trimethyl-1-cyclopentene The above-mentioned allyl ether (1.0 g, 5 mmole), together with tris(triphenylphosphine)ruthenium dichloride (6 mg, 0.12 mole %), was heated to 180°. After 75 min, the reaction mixture was distilled in a bulb-to-bulb apparatus to provide the desired (−)-(1'R)-2-methyl-4-(2',2',3'-trimethyl-3'-cyclopenten-1'-yl) -4-penten-1-al in a pure state (diastereomer mixture 2S/2R 55:45; yield 69%).

B.p.: 51°/9 Pa $[\alpha]^{20}{}_D$ (neat)=−72.0°

IR: 2960, 2710, 1730, 1640, 1460, 1360, 1120, 1015, 900 cm$^{-1}$

NMR($^1$H,360MHz, CDCl$_3$):

(1'R,2R): 0.77(s, 3H); 1.08(d, J=7, 3H); 1.10(s, 3H); 1.60(m,3H); 2.04(m,1H); 2.20(m,1H); 2.30(m,1H) ; 2.5(m,2H); 2.6(m, 1H); 4.91(s, 1H); 4.97(s, 1H); 5.28 (s, 1H); 9.66(d, J=2, 1H) δ ppm (1'R,2S): 0.76(s, 3H); 1.09(s, 3H); 1.11(d, J=7, 3H); 1.60(m, 3H); 2.04(m, 1H); 2.20(m, 1H); 2.30(m, 1H); 2.5(m, 2H); 2.6(m, 1H); 4.90(s, 1H); 4.96(s, 1H); 5.28(s, 1H); 9.62(d, J=2, 1H) δ ppm

NMR($^{13}$C):

(1'R,2R): 12.8(q); 13.4(q); 21.0(q); 27.1(q); 34.2(t); 38.1 (t); 44.7(d); 47.9(s); 55.5(d); 113.0(t); 121.5(d); 146.4 (s); 147.3(s); 204.7(d) δ ppm (1'R,2S): 12.8(q); 14.0(q); 21.0(q); 27.0(q); 34.1(t); 38.1(t); 44.9(d); 48.0(s); 56.3(d); 112.7(t); 121.5(d); 146.6(s); 147.3(s); 204.8(d) δ ppm

MS:

(1'R,2R): 206(M$^+$,7), 191(12), 173(21), 149(22), 133(59), 105(100), 91(98), 79(88), 67(43), 55(42), 41(38)

(1'R,2S): 206(M$^+$,8), 191(10), 73(18), 148(20), 133(59), 107(88), 91(100), 79(90), 67(51), 55(48), 41(41)

Odor: see above.

The aldehyde thus obtained was subsequently enriched in (2R) configuration diastereomer, via epimerisation by means of potassium tert-butoxide (3 g, 27 mmole), in tert-butanol (15 ml), at 20°–25°. After min, there was obtained a product wherein the ratio 2R/2S was 60:40.

This aldehyde was also obtained using another catalyst. Thus, a flask under nitrogen and equipped with a water separator was charged with 5% ruthenium on wet carbon (1.5 g; origin:Degussa), mesitylene (150 g) and the above-mentioned starting ether (50 g). The mixture was taken to reflux for 3 h. After filtering the catalyst and concentrating (100°/20×10$^2$ Pa), there was obtained the desired aldehyde.

The starting allyl ether was prepared as follows.

A mixture of (−)-(1'S)-2-(2',2',3'-trimethyl-3'-cyclopenten-1'-yl) -2-propen-1-ol ([α]$^{20}_D$ (neat)=−63.9°, 1.0 g, 6 mmole), allyl bromide (0.8 ml, 9 mmole) and NaOH (0.4 g, 9 mmole) was heated to reflux for 2 h. After extracting with ether and water to neutrality, drying over Na$_2$SO$_4$, concentrating and distilling in a bulb-to-bulb apparatus, there was obtained (−)-(S)-4-[1-(allyloxymethyl)ethenyl]-1,5,5-trimethyl-1-cyclopenten (purity: 99%; yield 83%), having the following analytical characters:

B.p.: 57°/0.6×10$^2$ Pa

[α]$^{20}_D$ (neat)=−60.55°

IR: 3040, 2960, 1645, 1450, 1360, 1090, 1020, 920 cm$^{-1}$

NMR($^1$H,360MHz,CDCl$_3$): 0.77(s, 3H); 1.08(s, 3H); 1.60 (q, J=2, 3H); 2.2–2.4(m, 2H); 2.60(t, J=7, 1H); 3.95(s, 2H); 3.99(m, 21H); 5.02(s, 2H); 5.18(m, 1H); 5.22(m, 1H); 5.30(m, 1H); 5.93(m, 1H) δ ppm NMR($^{13}$C): 12.8(q); 21.0(q); 26.8(q); 33.9(t); 47.7(s); ,53.5(d); 71.1(t); 73.6(t); 112.5(t); 116.7(t); 121.6(d); 135.0(d); 146.2(s); 147.4(s) δ ppm MS: 206(M$^+$,1), 133(90), 119(27), 105(100), 91(72), 79(53), 67(26), 57(27), 41(26)

Odor: cardamon, spicy, woody, lemon.

B. Starting from (−)-(S)-1,5,5-trimethyl-4-[1-(1-propenyloxymethyl) ethenyl]-1-cyclopentene The above-mentioned ether was heated to 180° during 90 min. After the usual treatment, there was obtained the desired aldehyde, having identical analytical characters to those described under A.

The starting ether was prepared as follows.

A mixture of (−)-(1'S)-2-(2',2',3'-trimethyl-3'-cyclopenten-1'-yl)-2-propen-1-ol (4.15 g, 25 mmole) and (CH$_3$COO)$_2$Hg (166 mg, 0.52 mmole) in solution in propenylethylether (12 g, 139 mmole) was taken to reflux during 48 h. The excess of propenylethylether and ethanol was distilled. The residue was distilled in a bulb-to-bulb apparatus in the presence of K$_2$CO$_3$ (332 mg) and under high vacuum, to provide 0.35 g of (−)-(S)-1,5,5-trimethyl-4-[1-(propenyloxymethyl)ethenyl]-1-cyclopentene (yield 7%) in the form of a mixture E/Z 1:4.

B.p.: 75°/1.3×10$^2$ Pa

[α]$^{20}_D$ (neat)=−46.4°

IR: 3040, 2980, 2940, 2880, 1660, 1450, 1180, 1140, 910, 800 cm$^{-1}$

NMR($^1$H,360MHz, CDCl$_3$):

Z: 0.69(s, 3H); 1.09(s, 3H); 1.60(d, J=2, 3H); 2.3(m, 2H); 2.58(t, J=7, 1H); 4.21(s, 2H); 4.4(quint, J=7, 1H); 5.03(m, 1H); 5.21(m, 1H); 5.28(s, 1H); 5.93(qd, J=2, 7, 1H) δ ppm E: 0.68(s, 3H); 1.07(s, 3H); 1.62(d, J=2, 3H); 2.3(m, 2H); 2.60(t, J=7, 1H); 4.11(s, 2H); 4.8(quint, J=7, 1H); 5.03(m, 1H); 5.21 (m, 1H); 5.28(s, 1H); 6.21(qd, J=2, 11, 1H) δ ppm NMR($^{13}$C): δ ppm Z: 9.3(q); 12.8(q); 20.9(q); 26.7(q); 33.8(t); 47.7(s); 53.4 (d); 75.0(t); 101(d); 112.8(t); 121.6(d); 145.4(d); 147.4 (s) δ ppm E: 12.6(q); 12.8(q); 20.9(q); 26.7(q); 33.8(t); 47.7(s); 53.6(d); 72.6(t); 99.2(d); 113.1(t); 121.6(d); 145.8(s); 146.3(d) δ ppm

MS:

Z: 206(M$^+$,8), 191(7), 149(16), 133(20), 121(25), 107 (92), 93(100), 79(50), 41(29)

E: 206(M$^+$,8), 191(10), 173(8), 148(16), 133(30), 121 (25), 107(86), 93(100), 79(50), 41(29)

EXAMPLE 2

Preparation of (+)-(1'S)-2-methyl-4-(2',2',3'-trimethyl-3'-cyclopenten-1'-yl)-4-penten-1-al This aldehyde was prepared in a similar manner to that described in Example 1, but starting from (+)-(1'R)-2-(2',2', 3'-trimethyl-3'-cyclopenten-1'-yl) -2-propen-1-ol ([α]$^{20}_D$ (neat)=+75.2°). The product obtained (mixture of diastereomers 2S/2R 52:48) had analytical characters identical to those of the aldehyde described in Example 1, with the exception of:

B.p.: 41°/3.2 Pa

[α]$^{20}_D$ (neat)=+82.7°

Odor:woody, sandalwood, aldehydic, faintly aqueous.

EXAMPLE 3

Preparation of (+)-(1'S)-4-(2',2',3'-trimethyl-3'-cyclopenten-1'-yl) -4-penten-1-al A. Preparation of (+)-(1'S)-4-(2',2',3'-trimethyl-3'-cyclopenten-1'-yl) -4-penten-1-ol A flask was charged with Celite® (52.5 g), pyridinium chlorochromate (PCC, 35 g, 0.162 mole) in 220 ml of dichloromethane. 21 g (0.108 mole) of (+)-(1'S)-4-(2',2',3'-trimethyl-3'-cyclopenten-1'-yl)-4-penten-1-ol in solution in 20 ml of CH$_2$Cl$_2$ were then introduced under nitrogen and mechanical stirring. After 1 h, the product was filtered on SiO$_2$ with ethyl ether, concentrated, washed with 15% HCl and then to neutrality with water, to provide, after evaporation and distillation in a bulb-to-bulb apparatus, 19.75 g (purity>99%; yield 95%) of the above-mentioned pentenal, with the following analytical characters:

B.p.: 60°/33 Pa

[α]$^{20}_D$ (neat)=+68.6°

IR: 2960, 1730, 1440, 900 cm$^{-1}$

NMR($^1$H,360MHz, CDCl$_3$): 0.75(s, 3H); 1.08(s, 3H); 1.59(q, J=2, 1H); 2.2–2.65(m, 7H); 4.83(d, J=2, 1H); 4.91(s, 1H); 5.27 (s large, 1H); 9.79(t, J=2, 1H) δ ppm NMR($^{13}$C): 12.8(q); 20.9(q); 27.0(q); 28.6(t); 33.9(t); 42.4(t); 48.0(s); 56.6(d); 111.2(t); 121.5(d); 147.3(s); 148.1(s); 202.3(d) δ ppm MS: 192(M$^+$,36), 177(28), 159(46), 133(80), 105(99), 91(100), 79(64), 55(44), 41(79)

Odor: see above.

The pentenol used as starting product above was obtained from (+)-(1'R)-2-(2',2',3'-trimethyl-3'-cyclopenten-1'-yl)-2-propen-1-ol following the method summarized in Scheme I. It presented the following analytical characters:

Purity: 98.8%
B.p.: 95.6°/13 Pa
$[\alpha]^{20}_D$ (neat)=+77.2°
IR: 3330, 2955, 1640, 1450, 1360, 1060, 890 cm$^{-1}$
NMR($^1$H,360MHz, CDCl$_3$): 0.74(s, 3H); 1.09(s, 3H); 1.59(q, J=2, 3H); 1.65(s large, 1H, OH); 1.74(quint, J=7, 2H); 2.05–2.25(m, 3H); 2.3–2.4(m, 1H); 2.55(t, J=7, 1H); 3.65(t, J=7, 2H); 4.85(s large, 1H); 4.91(d, J=2, 1H); 5.28(s large, 1H) δ ppm
NMR($^{13}$C): 12.8(q); 21.0(q); 27.0(q); 31.3(t); 32.9(t); 34.0(t); 47.9(s); 56.2(d); 62.8(t); 110.7(t); 121.6(d); 147.3(s); 149.5(s) d ppm
MS: 194(M$^+$,35), 179(28), 161(18), 135(99), 119(48), 107(93), 91(100), 79(60), 55(51), 41(92)
Odor: sandalwood.

B. Starting from (−)-(S)-1,5,5-trimethyl-4-[1-(vinyloxymethyl)ethenyl]-1-cyclopentene The above-mentioned vinylether was thermally treated in an analogous manner to that described in Example 1B, to provide the desired aldehyde, which presented identical analytical characters to those described under A.

The starting vinylether was prepared as follows.

A mixture of (−)-(1'S)-2-(2',2',3'-trimethyl-3'-cyclopenten-1'-yl)-2-propen-1-ol (4.15 g, 25 mmole) and Hg(CH$_3$COO)$_2$ (166 mg, 0.52 mmole) in solution in vinylethylether (12 g, 166 mmole) was taken to reflux during 20 h. The excess of vinylethylether was distilled, as well as the ethanol. The residue was distilled in a bulb-to-bulb apparatus in the presence of K$_2$CO$_3$ (332 mg), under high vacuum, to provide 2.21 g of (−)-(S)-1,5,5-trimethyl-4-[1-(vinyloxymethyl)ethenyl]-1-cyclopentene (yield 46%).

B.p.: 70°/5.3×10$^2$ Pa
$[\alpha]^{20}_D$ (neat)=−49.7°
IR: 3020, 2990, 2940, 2880, 1640, 1615, 1460, 1330, 1210, 920, 800 cm$^{-1}$
NMR($^1$H,360MHz,CDCl$_3$): 0.78(s, 3H); 1.08(s, 3H); 1.61 (q, J=2, 3H); 2.3(m, 2H); 2.62(t, J=7, 1H); 4.01(dd, J=2, 7, 1H); 4.18(s, 2H); 4.21(dd, J=2, 7, 1H); 5.07(s, 1H); 5.23(q, J=2, 1H); 5.29(s large, 1H); 6.47(dd, J=6, 12, 1H) δ ppm
NMR($^{13}$C): 12.8(q); 20.9(q); 26.7(q); 33.8(t); 47.7(s); 53.6(d); 71.5(t); 87.1(t); 113.3(t); 121.6(d); 144.9(s); 147.4(s); 151.6(d) δ ppm
MS: 192(M$^+$,5), 177(18), 159(14), 148(20), 133(88), 121 (25), 119(24), 105(90), 93(100), 91(95), 79(70), 55(32), 41(70)

EXAMPLE 4

Preparation of (−)-(1'R)-4-(2',2',3'-trimethyl-3'-cyclopenten-1'-yl)-4-penten-1-al Prepared analogously to its enantiomer described in Example 3 but starting from (−)-(1'R)-4-(2',2',3'-trimethyl-3'-cyclopenten-1'-yl) -4-penten-1-ol ($[\alpha]^{20}_D$ (neat)=−69.4°) or from (−)-(1'S)-2-(2',2',3'-trimethyl-3'-cyclopenten-1'-yl)-2-propen-1-ol. The compound obtained presented the same analytical characters as its enantiomer, excepting:

Purity: 97.6%
$[\alpha]^{20}_D$ (neat)=−66.3°
Odor: see above.

EXAMPLE 5

Preparation of (−)-(1'R,2S)-2-methyl-4-(2',2',3'-trimethyl-3'-cyclopenten-1'-yl)-4-pentenenitrile and of (−)-(1'R,2R)-2-methyl-4-(2',2',3'-trimethyl-3'-cyclopenten-1'-yl)-4-pentenenitrile A 500 ml flask equipped with a magnetic stirrer and kept under N$_2$, was charged with 22.27 g (0.32 mole) of hydroxylamine hydrochloride, 12.82 g (0.32 mole) of NaOH and 175 ml of ethanol. After heating to reflux, 60 g (0.29 mole) of (−)-(1'R)-2-methyl-4-(2',2',3'-trimethyl-3'-cyclopenten-1'-yl) -4-pentenal ($[\alpha]^{20}_D$=−52.8° (neat: see Example 1) were added dropwise and reflux continued for 1 h. After cooling, taking into ether, washing once with water, drying and concentrating, there were obtained 64.5 g of (−)-(1'R)-2-methyl-4-(2',2',3'-trimethyl-3'-cyclopenten-1'-yl) -4-pentenal oxime (mixture of 4 chiral isomers) having the following analytical characteristics:

$[\alpha]^{20}_D$=−52.2° (neat)
IR: 3300, 2959, 2360, 1457, 897 cm$^{-1}$
RMN($^1$H,360MHz): 0.75(s, 3H); 1.0–1.15(m,6H); 1.6 (broad s, 3H); 2.0–2.4(m, 4H); 2.45–2.7(m, 2H); 3.30–3.50(m, 1H); 4.88–4.97(m, 2H); 5.27(broad s, 1H); 6.49 and 6.53(2d, J=7, 9, 1H); 7.31 and 7.35(2d, J=6, 4, 1H) δ ppm
RMN($^{13}$C,360MHz): 12.81(q); 16.94; 17.43; 17.54; 18.15 (4q); 21.01(q); 26.90; 26.95(2q); 27.94; 28.14(2d); 32.89; 33.06(2d); 33.95; 34.04(2t); 41.57; 41.99; 42.26; 42.29(4t); 47.71; 47.75; 47.78; 47.81(4s); 55.35; 55.48; 55.65; 55.86(4d); 112.27; 112.59; 112.89; 113.20(4t); 121.52; 121.63; 121.68(3d); 146.43; 146.63; 147.19; 147.34(4s); 155.98; 156.13; 156.86; 157.06(4d) δ ppm
SM: isomer 1: 221 (2, M$^+$); 204(25), 188(16), 173(14), 160(16), 148(18), 138(59), 133(40), 119(36), 105(54), 91 (80), 79(70), 67(34), 55(45), 41(100), 28(45)
isomer 2: 221 (4, M$^+$); 204(39), 188(19), 173(18), 160 (21), 148(23), 138(91), 133(52), 119(47), 105(73), 91(100), 79(83), 67(39), 55(50), 41(98), 28(33)
isomer 3: 204(24), 188(16), 173(13), 160(15), 149(21), 133(36), 119(37), 117(12), 105(61), 91(92), 79(77), 67(33), 65(25), 55(45), 53(37), 51(18), 41(100), 39(64), 28(48)
isomer 4: 221 (1, M$^+$); 204(38), 188(14), 178(4), 173(13), 160(14), 149(18), 133(34), 119(34), 113(14), 105(58), 91(78), 79(72), 67(33), 55(41), 41(100), 28(35)
Odor: vaguely woody, sandalwood The oxime (64.5 g, 0.29 mole) thus obtained was charged into a flask together with 60 ml (0.63 mole) of acetic anhydride and the mixture was heated to reflux for 30 min. It was then allowed to cool, taken in ether, washed once with water, twice with 15% NaOH and again with water to neutrality. After drying and evaporation, there were obtained 56.6 g of raw product, which was further purified to provide (−)-(1'R)-2-methyl-4-(2',2',3'-trimethyl-3'-cyclopenten-1'-yl) 4-pentenenitrile (2R/2S 4:6) with the following characteristics:

Purity: >99%
$[\alpha]^{20}_D$=−63.4° (neat)

This product was subjected to chromatography on a silica column, using a mixture of cyclohexane/ethyl acetate 98:2 as eluting agent, to provide the two diastereomers in a pure state, having the following analytical characters:

(−)-(1'R,2R)-2-methyl-4-(2',2',3'-trimethyl-3'-cyclopenten-1'-yl) -4-pentenenitrile
Purity: 95%

[α]$^{20}_D$=−49.0° (neat)

IR: 2960, 1640, 1457, 1362, 902 cm$^{-1}$

RMN($^1$H,360MHz): 0.77(s, 3H); 1.09(s, 3H); 1.32(d, J=7, 3H); 1.61(broad s, 3H); 2.27(m, 3H); 2.45(dxd, J$_1$=8, J$_2$=5, H); 2.53(t, J=9, 1H); 2.77(sext, J=7, 1H)); 5.04 (broad s, 1H); 5.06(broad s, 1H); 5.27(broad s, 1H) δ ppm RMN($^{13}$C,360MHz): 12.9(q); 17.9(q); 21.0(q); 24.5(d); 26.8(q); 34.0(t); 40.8(t); 48.1(s); 55.9(d); 114.3(t); 121.3(d); 123.0(s); 144.9(s); 147.4(s) δ ppm SM: 203(32,M$^+$); 188(78), 173(16), 160(94), 146(22), 133(60), 119(38), 105(92), 91(88), 79(100), 67(28), 55(30), 41(66), 27(24).

(−)-(1'R,2R)-2-methyl-4-(2',2',3'-trimethyl-3'-cyclopenten-1'-yl) -4-pentenenitrile Purity: 95%

[α]$^{20}_D$=−65.9° (neat)

IR: 2960, 1640, 1457, 1362, 901 cm$^{-1}$

RMN($^1$H,360MHz): 0.77(s, 3H); 1.08(s, 3H); 1.36(d, J=7, 3H); 1.60(broad s, 3H); 2.24(dxd, J$_1$=5, J$_2$=15, 1H); 2.30(m, 2H); 2.43(dxd, J$_1$=9, J$_2$=15, 1H); 2.52(t, J=9, 1H); 2.82(m, 1H); 5.05(broad s, 1H); 5.07(broad s, 1H); 5.28(broad s, 1H) δ ppm RMN($^{13}$C,360MHz): 12.8(q); 18.2(q); 21.0(q); 24.8(d); 27.0(q); 34.1(0; 41.2(t); 48.0(s); 55.8(d); 114.0(t); 121.6(d); 122.0(s); 145.1(s); 147.2(s) δ ppm SM: 203(32,M$^+$); 188(76), 173(17), 160(92), 146(21), 133(60), 119(37), 105(89), 91(86), 79(100), 67(28), 55(30), 41(63), 27(20)

EXAMPLE 6

Preparation of (−)-(1'R)-2-methyl-4-(2',2',3'-trimethyl-3'-cyclopenten-1'-yl) -4-penten-1-ol Ethanol (40 ml) and then NaBH$_4$ (235 mg, 6 mmole) were added to the aldehyde obtained according to Example 1 (2R/2S 60:40). After 45 min, the product was poured on ice for hydrolysis, extracted with 30/50 petroleum ether washed to neutrality with water, dried, concentrated and distilled to provide the desired pentenol in the form of a mixture of 2 diastereomers 2R/2S 55: 45 (yield 77%).

The product thus obtained had similar analytical characters to those described in the prior art, excepting:

[α]$^{20}_D$(neat)=−69.7°

The two diastereomers present in this mixture were separated by flash chromatography on 230 g of SiO$_2$, using as eluting agent a 95:5 mixture of cyclohexane/ethyl acetate. There were thus obtained:

(−)-(1'R,2S)-2-methyl-4-(2',2',3'-trimethyl-3'-cyclopenten-1'-yl) -4-penten-1-ol (purity 93% )

[α]$^{20}_D$=−55.7°; c=1.2, CHCl$_3$ (−)-(1'R,2R)-2-methyl-4-(2',2',3'-trimethyl-3'-cyclopenten-1'-yl) -4-penten-1-ol (purity 70%)

[α]$^{20}_D$=−75.4°; c=1.4, CHCl$_3$

Chromatographic separation of the same mixture on a Carbowax® 20 M type column, 15%, 15 m, 0.25 mm of diameter, at 160° made it possible to obtain said diastereomers with the following characteristics:

(−)-(1'R,2S)

R$_t$=7.2 min

[α]$^{20}_D$=−60.8°; c=0.6, CCl$_4$

NMR($^1$H,360MHz, CDCl$_3$): 0.76(s, 3H); 0.96(d, J=7, 3H); 1.10(s, 3H); 1.5(s large, 1H, OH); 1.61(s large, 3H); 1.9–2.04(m, 2H); 2.12–2.23(m, 2H); 2.30–2.39 (m, 1H); 2.59(t, J=7, 1H); 3.43(dd, J=10, 6, 1H); 3.54(dd, J=10, 6, 1H); 4.92(s, 1H); 4.95(s, 1H); 5.28(s, 1H) δ ppm NMR($^{13}$C): 12.8(q); 17.3(q); 21.0(q); 27.0(q); 34.2(t); 34.2(d); 41.9(t); 47.8(s); 55.7(d); 68.1(t); 112.0(t); 121.6(d); 147.4(s); 148.6(s) δ ppm (−)-(1'R,2R)

R$_t$=7.6 min

[α]$^{20}_D$=−73.1°; c=0.5, CCl$_4$

NMR($^1$H,360MHz, CDCl$_3$): 0.76(s, 3H); 0.89(d, J=7, 3H); 1.10(s, 3H); 1.58(s large, 1H); 1.61(d, J=2, 3H); 1.8–1.97(m, 2H); 2.12–2.40(m, 3H); 2.54(t, J=8, 1H); 3.48(dd, J=10, 5, 1H); 3.54(dd, J=10, 5, 1H); 4.92(s, 2H); 5.28(s, 1H) δ ppm NMR($^{13}$C): 12.8(q); 16.3(q); 21.0(q); 27.0(q); 34.2(d); 34.3(t); 41.4(t); 47.8(s); 55.2(d); 68.6(t); 112.1(t); 121.6(d); 147.4(s); 148.0(s) δ ppm

EXAMPLE 7

Preparation of (+)-(1'S)-2-methyl-4-(2',2',3'-trimethyl-3'-cyclopenten-1'-yl) -4-penten-1-ol Obtained from the aldehyde described in Example 2, following the procedure described in Example 6. The desired pentenol was obtained in the form of a mixture of diastereomers 2R/2S 55: 45 and [α]$^{20}_D$ (neat)=+79.1°. The two diastereomers were separated by gas chromatography on a column of the type Carbowax® 20 M, 15%, 6 m, 6 mm of diameter, at 180°.

(+)-(1'S,2S)-2-methyl-4-(2',2',3'-trimethyl-3'-cyclopenten-1'-yl) -4-penten-1-ol

[α]$^{20}_D$=+67.6°; c=0.15, CCl$_4$ (+)-(1'S,2R)-2-methyl-4-(2',2',3'-trimethyl-3'-cyclopenten-1'-yl) -4-penten-1-ol

[α]$^{20}_D$=+71.7°; c=1.0, CCl$_4$

EXAMPLE 8

Preparation of a perfuming composition

A base perfuming composition was prepared by admixing the following ingredients:

| Ingredients | Parts by weight |
| --- | --- |
| Benzyl acetate | 20 |
| Geranyl acetate | 5 |
| Styrallyl acetate | 5 |
| Hexylcinnamic aldehyde | 20 |
| 10%* Amyl allyl glycolate | 30 |
| Bergamot essential oil | 90 |
| Lemon essential oil | 10 |
| Citronellol | 10 |
| Coumarine | 35 |
| Dihydromyrcenol [1] | 5 |
| Galaxolide ® [2] 50 | 20 |
| Geraniol | 5 |
| Hedione ® [3] | 140 |
| 10%* Indol | 5 |
| Isoeugenol | 5 |
| Jasmin absolute | 20 |
| α-Isomethylionone | 110 |
| Muscone | 25 |
| Nerol | 5 |
| 1%* p-Cresol | 20 |
| Phenethylol | 10 |
| Capsicum berries essential oil | 10 |
| Benzyl salicylate | 15 |
| Hexyl salicylate | 10 |
| Pipol salicylate | 10 |

-continued

| Ingredients | Parts by weight |
|---|---|
| Sandalwood essential oil | 190 |
| Undecalactone | 5 |
| 10%* Vanilline | 25 |
| Ylang essential oil | 40 |
| Total | 900 |

*in dipropyleneglycol (DIPG)
[1] 2,6-dimethyl-7-octen-2-ol; origin: International Flavors & Fragrances, USA
[2] 1,3,6,7-hexahydro-4,6,6,7,8,8-hexamethyl-cyclopenta[g]isochromene; origin: International Flavors & Fragrances, USA
[3] methyl dihydrojasmonate; origin: Firmenich SA, Geneva, Switzerland To this base composition of the woody, oriental type there were added 100 parts by weight of (−)-(1'R)-2-methyl-4-(2', 2',3'-trimethyl-3'-cyclopenten-1'-yl)-4-penten-1-al. The novel composition thus obtained developed an odor wherein the sandalwood note was distinctly exhalted relative to that of the base composition and which possessed in addition a very fresh and powerful headnote. Furthermore, an ozony, marine and aldehydic connotation could now be clearly perceived, which was totally absent from the odor of the base composition.

When the same amount of (+)-(1'S)-2-methyl-4-(2',2',3'-trimethyl-3'-cyclopenten-1'-yl)-4-penten-1-al was added to the base composition, a similar exhalting effect of the sandalwood note was observed, the novel composition having also acquired an aldehydic-metallic character, but the marine character was no longer present.

Upon adding to the base composition 100 parts by weight of (+)-(1'R)-4-(2',2',3'-trimethyl-3'-cyclopenten-1'-yl)-4-penten-1-al, no enhancement of the sandalwood note was observed, but the composition had then acquired a distinctly more floral and greener connotation, and the citrus undernote had also become much stronger.

The addition to the base composition of the same amount of (−)-(1'S)-4-(2',2',3'-trimethyl-3'-cyclopenten-1'-yl)-4-penten-1-al clearly weakened the sandalwood character of the composition, which had then acquired a far more aldehydic and almost soapy connotation.

EXAMPLE 9

Preparation of a perfuming composition

A base perfuming composition was prepared by admixing the following ingredients:

| Ingredients | Parts by weight |
|---|---|
| Benzyl acetate | 100 |
| Pipol acetate | 10 |
| Hexylcinnamic aldehyde | 110 |
| Cinnamic alcohol | 200 |
| 10%* Galbanum essential oil | 30 |
| Hedione ® [1] | 40 |
| 10%* Indol | 25 |
| Methyl jasmonate | 10 |
| Methylisoeugenol | 65 |
| Mayol ® [2] | 25 |
| 1-(5,5-Dimethyl-1-cyclohexen-1-yl)-4-penten-1-one [3] | 55 |
| Phenethylol | 215 |
| 10%* (Z)-3-Hexen-1-ol | 20 |
| α-Terpineol | 20 |
| 10%* Zestover ® [4] | 25 |

| Ingredients | Parts by weight |
|---|---|
| Total | 950 |

*in dipropylene glycol
[1] see preceding example
[2] cis-4-(1-methylethyl)-cyclohexanol; origin: Firmenich SA, Geneva, Switzerland
[3] Neobutenone ® ; origin: Firmenich SA, Geneva, Switzerland
[4] 2,4-dimethyl-3-cyclohexene-1-carbaldehyde; origin: Firmenich SA, Geneva, Switzerland To this base composition of the floral-hyacinth type, there were added 50 parts by weight of (−)-(1'R)-2-methyl-4-(2', 2',3'-trimethyl-3'-cyclopenten-1'-yl)-4-penten-1-al to provide a novel composition, the green note of which had become far more aqueous and fresh than that of the base composition and was now also accompanied by a very natural woody undernote. This fresh, marine effect was no longer observed when the same amount of (+)-(1'S)-2-methyl-4-(2',2',3'-trimethyl-3'-cyclopenten-1'-yl)-4-penten-1-al was added to the base composition.

The addition to the base composition of 50 parts by weight of (−)-(1'R)-4-(2',2',3'-trimethyl-3'-cyclopenten-1'-yl) -4-penten-1-al imparted to it a more spicy character and added a slightly metallic connotation, faintly citronella. On the other hand, (+)-(1'S)-4-(2',2',3'-trimethyl-3'-cyclopenten-1'-yl)-4-penten-1-al, when added in the same amount, improved the odor quality of the composition by enhancing the green notes, which are then accompanied of a slightly metallic aspect.

When 50 parts by weight of (−)-(1'R,2R)-2-methyl-4-(2', 2',3'-trimethyl-3'-cyclopenten-1'-yl)-4-pentenenitrile were added to the same base composition, a novel composition was obtained having a character quite distinct from that of the above-mentioned compositions, its odor being far more earthy, less green and woody, with a citrus aspect. The addition of this compound toned down the floral character of the base compound, while imparting an odor character distinctly more similar to the odor of hyacinth absolute.

EXAMPLE 10

Preparation of a perfuming composition

A base perfuming composition was prepared by admixing the following ingredients:

| Ingredients | Parts by weight |
|---|---|
| 10%* Decyl aldehyde | 10 |
| 10%* Undecylenic aldehyde | 40 |
| 10%* Dodecyl aldehyde | 10 |
| 10%* Methylnonylacetic aldehyde | 10 |
| 10%* Angelica roots essential oil | 10 |
| 10%* Castoreum | 20 |
| 10%* Defatted natural civet | 10 |
| Galbanum resinoid | 10 |
| 50%* Jasmine absolute | 100 |
| Oliban essential oil | 10 |
| Patchouli essential oil | 30 |
| Styrallyl acetate | 15 |
| α-Isomethylionone | 95 |
| Coriander essential oil | 5 |
| Hydroxycitronellol | 65 |
| 10%* Cyclopentadecanolide | 50 |
| Synth. jasmine oil | 100 |
| Synth. bergamot oil | 100 |
| Synth. lemon oil | 40 |
| 50%* Oakmoss absolute | 30 |

-continued

| Ingredients | Parts by weight |
| --- | --- |
| Synth. neroli oil | 20 |
| 10%* Muscone | 50 |
| Coumarine | 50 |
| Musk ambrette | 10 |
| Musk ketone | 30 |
| Diethyl phthalate | 50 |
| Total | 970 |

*in diethyl phthalate

To 98 g of this base composition of the woody-animal type, there were added 2 g of each of the chiral isomers of 2-methyl-4-(2',2',3'-trimethyl-3'-cyclopenten-1'-yl)-4-penten-1-ol indicated in the Table hereinafter, to prepare the four B to E perfuming compositions.

TABLE

| Composition | Isomer |
| --- | --- |
| A | (−)-(1'R) |
| B | (−)-(1'R,2R) |
| C | (−)-(1'R,2S) |
| D | (+)-(1'S,2S) |
| E | (+)-(1'S,2R) |

The four compositions B to E were then evaluated on a blind test by a panel of expert perfumers, who were expected to give their opinion on the quality of the odor, its strength and its analogy to the natural sandalwood oil.

The perfumers unanimously chose composition B as being the one which possessed the most powerful and natural sandalwood odor, with a neat "lait de santal" character and a very elegant fragrance. As for the three other compositions, composition C was rated second, although its sandalwood odor was judged to have a clearly less natural character, less "lait de santal" and possessing a cedar quality which was not present in the odor of composition B. On the other hand, regarding compositions D and E the opinions were divided, and the only general consensus was that they were not substantially different from the base composition, from an olfactive point of view.

When the same panel was asked to evaluate composition B vis-a-vis composition A, again there was a clear preference for composition B, the odor of which was judged more powerful and natural, with a more elegant sandalwood character.

What we claim is:

1. A compound of formula

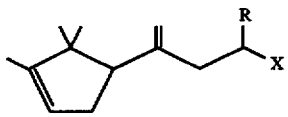

(I)

wherein R represents a hydrogen atom or a methyl radical and X stands for a —CHO or a —CN group.

2. An optically active isomer selected from the group consisting of:

(a) (−)-(1'R)-2-methyl-4-(2',2',3'-trimethyl-3'-cyclopenten-1'-yl)-4-penten-1-al;

(b) (+)-(1'S)-2-methyl-4-(2',2',3'-trimethyl-3'-cyclopenten-1'-yl)-4-penten-1-al;

(c) (−)-(1'R)-4-(2',2',3'-trimethyl-3'-cyclopenten-1'-yl)-4-penten-1-al;

(d) (+)-(1'S)-4-(2',2',3'-trimethyl-3'-cyclopenten-1'-yl)-4-penten-1-al;

(e) (−)-(1'R,2S)-2-methyl-4-(2',2',3'-trimethyl-3'-cyclopenten-1'-yl)-4-pentenenitrile; and (f) (−)-(1'R,2R)-2-methyl-4-(2',2',3'-trimethyl-3'-cyclopenten-1'-yl)-4-pentenenitrile.

3. A mixture of any two or more compounds selected in the group defined in claim 2.

4. The optically active isomer of claim 2 selected from the group consisting of:

(a) (−)-(1'R)-4-(2',2',3'-trimethyl-3'-cyclopenten-1'-yl)-4-penten-1-al;

(b) (+)-(1'S)-4-(2',2',3'-trimethyl-3'-cyclopenten-1'-yl)-4-penten-1-al;

(c) (−)-(1'R,2S)-2-methyl-4-(2',2',3'-trimethyl-3'-cyclopenten-1'-yl)-4-pentenenitrile; and (d) (−)-(1'R,2R)-2-methyl-4-(2',2',3'-trimethyl-3'-cyclopenten-1'-yl)-4-pentenenitrile.

5. 2-Methyl-4-(2,2,3-trimethyl-3-cyclopenten-1-yl)-4-pentenal oxime.

6. A perfuming composition or a perfumed article, containing as a perfuming ingredient a compound according to claim 1.

7. A perfuming composition or a perfumed article according to claim 6, wherein said compound is selected from the group consisting of:

(a) (−)-(1'R)-2-methyl-4-(2',2',3'-trimethyl-3'-cyclopenten-1'-yl)-4-penten-1-al;

(b) (+)-(1'S)-2-methyl-4-(2',2',3'-trimethyl-3'-cyclopenten-1'-yl)-4-penten-1-al;

(c) (−)-(1'R)-4-(2',2',3'-trimethyl-3'-cyclopenten-1'-yl)-4-penten-1-al;

(d) (+)-(1'S)-4-(2',2',3'-trimethyl-3'-cyclopenten-1'-yl)-4-penten-1-al;

(e) (−)-(1'R,2S)-2-methyl-4-(2',2',3'-trimethyl-3'-cyclopenten-1'-yl)-4-pentenenitrile; and (f) (−)-(1'R,2R)-2-methyl-4-(2',2',3'-trimethyl-3'-cyclopenten-1'-yl)-4-pentenenitrile.

8. A perfumed article according to claim 6, in the form of a perfume or a cologne, a soap, a bath or shower gel, a cosmetic preparation, a shampoo or other hair-care product, a body deodorant or an air-freshener, a detergent, a fabric softener or a household product.

9. A composition comprising a compound of formula

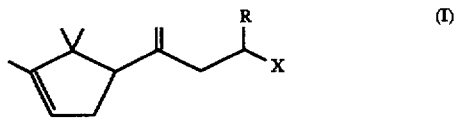

(I)

wherein R represents a hydrogen atom or a methyl radical and X is a —CN group.

10. The composition of claim 9 wherein said compound is selected from the group consisting of (−)-(1'R,2S)-2-methyl-4-(2',2',3'-trimethyl-3'-cyclopenten-1'-yl)-4-pentenenitrile and (−)-(1'R,2R)-2-methyl-4-(2',2',3'-trimethyl-3'-cyclopenten-1'-yl)-4-pentenenitrile.

11. A method to confer, improve, enhance or modify the odor properties of a perfuming composition or a perfumed article, which method comprises adding thereto a compound according to claim 1.

12. The method of claim 11, which comprises adding a compound selected from the group consisting of:

(a) (−)-(1'R)-2-methyl-4-(2',2',3'-trimethyl-3'-cyclopenten-1'-yl)-4-penten-1-al;

(b) (+)-(1'S)-2-methyl-4-(2',2',3'-trimethyl-3'-cyclopenten-1'-yl)-4-penten-1-al;

(c) (−)-(1'R)-4-(2',2',3'-trimethyl-3'-cyclopenten-1'-yl)-4-penten-1-al;

(d) (+)-(1'S)-4-(2',2',3'-trimethyl-3'-cyclopenten-1'-yl)-4-penten-1-al;

(e) (−)-(1'R,2S)-2-methyl-4-(2',2',3'-trimethyl-3'-cyclopenten-1'-yl)-4-pentenenitrile; and (f) (−)-(1'R,2R)-2-methyl-4-(2',2',3'-trimethyl-3'-cyclopenten-1'-yl)-4-pentenenitrile.

13. A method to confer, improve, enhance or modify the sandalwood, marine, ozone type odor character of a perfuming composition or a perfumed article, which method comprises adding thereto a compound of (−)-(1'R)-2-methyl-4-(2', 2', 3'-trimethyl-3'-cyclopenten-1'-yl)-4-penten-1-al or (+)-(1'S)-4-(2',2',3'-trimethyl-3'-cyclopenten-1'-yl)-4-penten-1-al in an amount sufficient to achieve the fragrant effect.

* * * * *